(12) United States Patent
Liu et al.

(10) Patent No.: US 12,136,697 B2
(45) Date of Patent: Nov. 5, 2024

(54) ELECTROLYTE AND ELECTROCHEMICAL APPARATUS

(71) Applicant: NINGDE AMEPEREX TECHNOLOGY LIMITED, Ningde (CN)

(72) Inventors: Junfei Liu, Fujian (CN); Jianming Zheng, Fujian (CN); Chao Tang, Fujian (CN); Lilan Zhang, Fujian (CN)

(73) Assignee: NINGDE AMEPEREX TECHNOLOGY LIMITED, Ningde (CN)

( * ) Notice: Subject to any disclaimer, the term of this patent is extended or adjusted under 35 U.S.C. 154(b) by 593 days.

(21) Appl. No.: 17/281,882

(22) PCT Filed: Mar. 27, 2020

(86) PCT No.: PCT/CN2020/081788
§ 371 (c)(1),
(2) Date: Mar. 31, 2021

(87) PCT Pub. No.: WO2021/189449
PCT Pub. Date: Sep. 30, 2021

(65) Prior Publication Data
US 2022/0216515 A1    Jul. 7, 2022

(51) Int. Cl.
*H01M 10/0567* (2010.01)
*C07D 327/04* (2006.01)
(Continued)

(52) U.S. Cl.
CPC ...... *H01M 10/0567* (2013.01); *C07D 327/04* (2013.01); *H01M 4/0404* (2013.01);
(Continued)

(58) Field of Classification Search
CPC .......... H01M 10/0567; H01M 4/0404; H01M 4/525; H01M 10/0525; H01M 10/0568;
(Continued)

(56) References Cited

U.S. PATENT DOCUMENTS 10,243,206 B2  3/2019 Zheng et al.
2004/0096750 A1*  5/2004 Kim ................... H01M 4/5815
                                                   429/231.95
(Continued)

FOREIGN PATENT DOCUMENTS

CN    101882679    11/2010
CN    102790236    11/2012
(Continued)

OTHER PUBLICATIONS

Liu, Junfei; International Search Report and Written Opinion for PCT/CN2020/081788, filed Mar. 27, 2020, mailed Jan. 4, 2021, 8 pgs.
(Continued)

*Primary Examiner* — Daniel S Gatewood
(74) *Attorney, Agent, or Firm* — Maier & Maier, PLLC

(57) ABSTRACT

An electrochemical apparatus, including a positive electrode, a negative electrode, an separator, and an electrolyte, wherein the positive electrode comprises a current collector
(Continued)

and a positive active material layer, and the positive active material layer comprises a positive active material; and the electrolyte comprises a compound of Formula I:

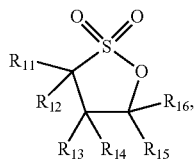

Formula I wherein $R_{11}$, $R_{12}$, $R_{13}$, $R_{14}$, $R_{15}$ and $R_{16}$ are each independently selected from: H, halogen, and the following substituted or unsubstituted groups: a $C_{1-8}$ alkyl group, a $C_{2-8}$ alkenyl group, a $C_{2-8}$ alkynyl group, or a $C_{6-12}$ aryl group; and an amount of the compound of Formula I required per 1 g of the positive active material is about 0.001 g to about 0.064 g. The present application can effectively improve high-temperature storage and high-temperature cycle performance of an electrochemical apparatus.

15 Claims, 1 Drawing Sheet

(51) Int. Cl.
| | |
|---|---|
| *H01M 4/02* | (2006.01) |
| *H01M 4/04* | (2006.01) |
| *H01M 4/525* | (2010.01) |
| *H01M 10/0525* | (2010.01) |
| *H01M 10/0568* | (2010.01) |
| *H01M 10/0569* | (2010.01) |

(52) U.S. Cl.
CPC ....... *H01M 4/525* (2013.01); *H01M 10/0525* (2013.01); *H01M 10/0568* (2013.01); *H01M 10/0569* (2013.01); *H01M 2004/021* (2013.01); *H01M 2004/028* (2013.01)

(58) Field of Classification Search
CPC ....... H01M 10/0569; H01M 2004/021; H01M 2004/028; H01M 10/4235; H01M 4/131; H01M 4/364; H01M 2300/0042; H01M 4/62; H01M 4/366; H01M 4/505; H01M 10/052; C07D 327/04; Y02E 60/10
See application file for complete search history.

(56) References Cited

U.S. PATENT DOCUMENTS

| | | | |
|---|---|---|---|
| 2017/0301952 A1* | 10/2017 | Changlong | H01M 10/0525 |
| 2017/0346127 A1* | 11/2017 | Zhang | H01M 4/131 |
| 2019/0044184 A1* | 2/2019 | Takada | H01M 4/525 |

FOREIGN PATENT DOCUMENTS

| | | |
|---|---|---|
| CN | 104979589 | 10/2015 |
| CN | 105702947 A | 6/2016 |
| CN | 106025359 | 10/2016 |
| CN | 106133988 A | 11/2016 |
| CN | 106602131 | 4/2017 |
| CN | 108701863 | 10/2018 |
| CN | 109273767 A | 1/2019 |
| CN | 109494354 | 3/2019 |
| CN | 109980225 A | 7/2019 |
| CN | 110165219 A | 8/2019 |
| CN | 110660962 | 1/2020 |
| CN | 105845983 | 2/2020 |
| EP | 2485316 A1 | 8/2012 |
| EP | 3454396 A1 | 3/2019 |
| EP | 3576189 A1 | 12/2019 |
| JP | 2006004649 A | 1/2006 |
| JP | 2007294397 A | 11/2007 |
| JP | 2009283353 | 12/2009 |
| JP | 2009283353 A * | 12/2009 |
| JP | 2012174340 A | 9/2012 |
| JP | 2014135296 A | 7/2014 |
| JP | 2014160568 A | 9/2014 |
| JP | 201592454 A | 5/2015 |
| JP | 2015191849 A | 11/2015 |
| JP | 202031020 A | 2/2020 |
| KR | 1020130130844 A | 12/2013 |
| KR | 1020150063954 A | 6/2015 |
| KR | 1020180013103 A | 2/2018 |
| WO | 2016025589 A1 | 2/2016 |
| WO | 2016121935 A1 | 8/2016 |

OTHER PUBLICATIONS

Liu, Junfei; Office Action for Chinese patent application No. 202010233604.6, mailed Dec. 15, 2020, 9 pgs.
Examination Report issued on Nov. 17, 2022, in corresponding Indian Application No. 202117017482, 5 pages.
Office Action issued on Jul. 19, 2022, in corresponding Japanese Application No. 2021-523465, 6 pages.
Office Action issued on Nov. 22, 2022, in corresponding Japanese Application No. 2021-523465, 6 pages.
Decision to Grant a Patent issued on Jun. 13, 2023, in corresponding Japanese Application No. 2021-523465, 2 pages.
Office Action issued on Jun. 21, 2023, in corresponding Korean Application No. 10-2021-7012961, 16 pages.
Extended European Search Report issued on Mar. 30, 2022, in corresponding European Application No. 20920752.1, 12 pages.
Office Action issued on Aug. 30, 2024, in corresponding Chinese Application No. 202110324283.5, 14 pages.

* cited by examiner

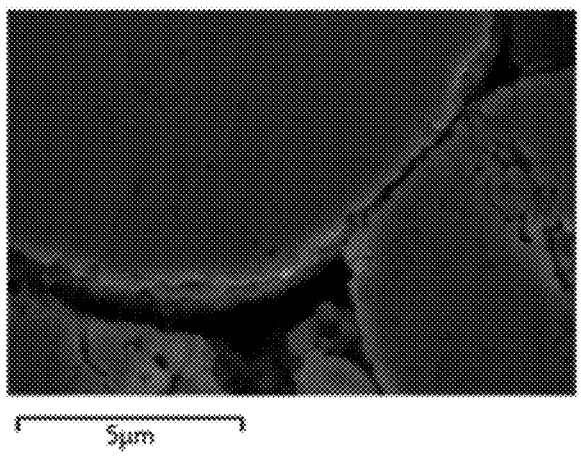
Electron micrograph 4
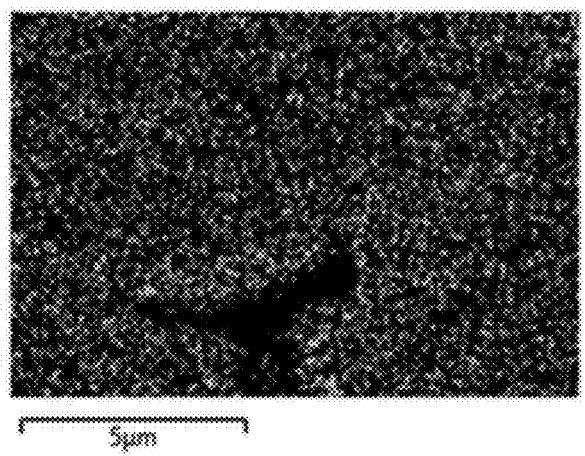
P Kα1

ELECTROLYTE AND ELECTROCHEMICAL APPARATUS

CROSS-REFERENCE TO RELATED APPLICATIONS

The present application is a National Stage application of PCT international application: PCT/CN2020/081788, filed on Mar. 27, 2020, the disclosure of which is hereby incorporated by reference in its entirety.

TECHNICAL FIELD

The present application relates to the field of energy storage technologies, and in particular, to an electrolyte and an electrochemical apparatus containing the electrolyte.

BACKGROUND

As a chemical power source, lithium-ion batteries have advantages such as high energy density, high working voltage, light weight, low self-discharge rate, long cycle life, no memory effect and environmental friendliness, and have been widely used in intelligent products (including mobile phones, laptops, cameras and other electronic products), electric vehicles, electric tools, drones, intelligent robots, advanced weapons and large-scale energy storage and other fields and industries. However, with the rapid development of information and communication technology and the diversity of market demands, people also put forward more requirements and challenges for the power supply for electronic products, for example, being thinner and lighter, more diverse shapes, higher volumetric energy density and mass energy density, higher safety, and higher power.

SUMMARY

The present application provides an electrolyte and an electrochemical apparatus which are capable of improving high-temperature cycle performance, high-temperature storage performance and provide higher safety performance.

The present application provides an electrochemical apparatus including a positive electrode, a negative electrode, a separator and an electrolyte, where the positive electrode includes a current collector and a positive active material layer, and the positive active material layer includes a positive active material; and the electrolyte includes a compound of Formula I:

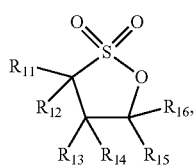

Formula I where $R_{11}$, $R_{12}$, $R_{13}$, $R_{14}$, $R_{15}$ and $R_{16}$ are each independently selected from: H, halogen, and the following substituted or unsubstituted groups: a $C_{1-8}$ alkyl group, a $C_{2-8}$ alkenyl group, a $C_{2-8}$ alkynyl group, or a $C_{6-12}$ aryl group; and an amount of the compound of Formula I per 1 g of the positive active material is about 0.001 g to about 0.064 g.

In some embodiments, the compound of Formula I includes at least one of the following compounds:

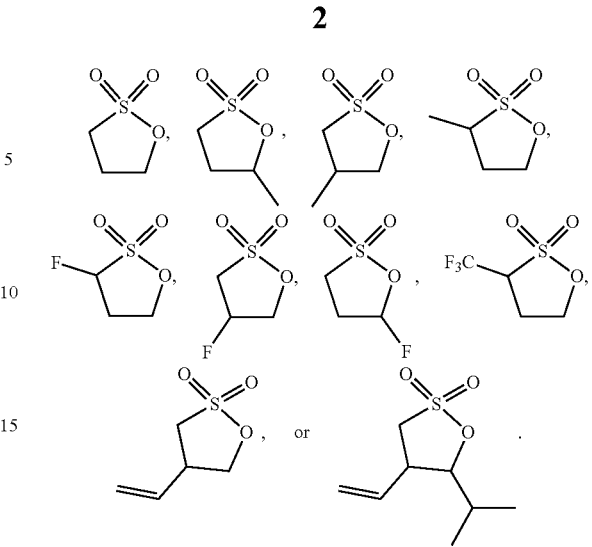

In some embodiments, the positive active material layer includes first particles, and a roundness of the first particles is 0.4 to 1, and with respect to a cross-sectional area of the positive electrode perpendicular to the current collector, a cross-sectional area of the first particle is greater than or equal to 20 square microns, and a sum of the cross-sectional areas of the first particles is 5% to 50% of a cross-sectional area of positive electrode.

In some embodiments, the positive active material layer includes second particles, and a roundness of the second particles is less than 0.4, and with respect to the cross-sectional area of the positive electrode perpendicular to the current collector, a cross-sectional area of the second particle is less than a cross-sectional area of the first particle.

In some embodiments, with respect to the cross-sectional area of the positive electrode perpendicular to the current collector, a sum of the cross-sectional areas of the second particles is 5% to 60% of the cross-sectional area of positive electrode.

In some embodiments, the electrolyte further includes an additive A, and the additive A includes at least one of $LiBF_4$, $LiPO_2F_2$, LiFSI, LiTFSI, 4,5-dicyano-2-trifluoromethylimidazolium, lithium difluoro bis (oxalate) phosphate, lithium difluoroacetate borate, or lithium bisoxalate borate.

In some embodiments, an amount of the additive A is 0.000026 g to 0.019 g per 1 g of the positive active material.

In some embodiments, the electrolyte further includes an additive B, and the additive B includes at least one of vinylene carbonate (VC), fluoroethylene carbonate (FEC), ethylene sulfate (DTD), tris(trimethylsilyl) phosphate (TMSP), tris(trimethylsilyl) borate (TMSB), adiponitrile (ADN), succinonitrile (SN), 1, 3, 5-pentanetricarbonitrile, 1, 3, 6-hexanetricarbonitrile (HTCN), 1, 2, 6-hexanetricarbonitrile, or 1, 2, 3-tris(2-cyanoethoxy)propane (TECP).

In some embodiments, a mass ratio of the compound of Formula I to the additive B is about 7:1 to about 1:7.

In some embodiments, an amount of the additive B is 0.0001 g to 0.2 g per 1 g of the positive active material.

In some embodiments, the positive active material layer includes a phosphorus-containing compound, and the phosphorus-containing compound includes at least one of $Li_3PO_4$ or $LiMPO_4$, where M is selected from at least one of Co, Mn, or Fe.

In some embodiments, the phosphorous-containing compound is contained in a surface or a grain boundary of the positive active material.

In some embodiments, the positive active material includes $LiNi_xCo_yMn_zO_2$, where $0.55<x<0.92$, $0.03<y<0.2$, and $0.04<z<0.3$.

In some embodiments, the positive active material includes an element Q, and the Q is selected from at least one of Zr, Ti, Yr, V, Al, Mg, or Sn.

In some embodiments, a porosity of the positive electrode is ≤25%.

In some embodiments, with respect to the cross-sectional area of the positive electrode perpendicular to the current collector, a cross-sectional area of the positive current collector takes up a proportion of 5% to 20%.

In some embodiments, a compacted density of the positive active material layer is less than or equal to 3.6 $g/cm^3$.

In some embodiments, the electrolyte further includes a compound of Formula II:

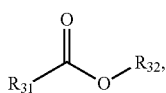

Formula II where $R_{31}$ and $R_{32}$ are each independently selected from a substituted or unsubstituted $C_{1-10}$ alkyl group, or a substituted or unsubstituted $C_{2-8}$ alkenyl group, where being substituted refers to substitution with one or more halogen atoms; and based on a total weight of the electrolyte, a content of the compound of Formula II is 0.5 wt % to 50 wt %.

In some embodiments, the compound of Formula II includes at least one of the following compounds:

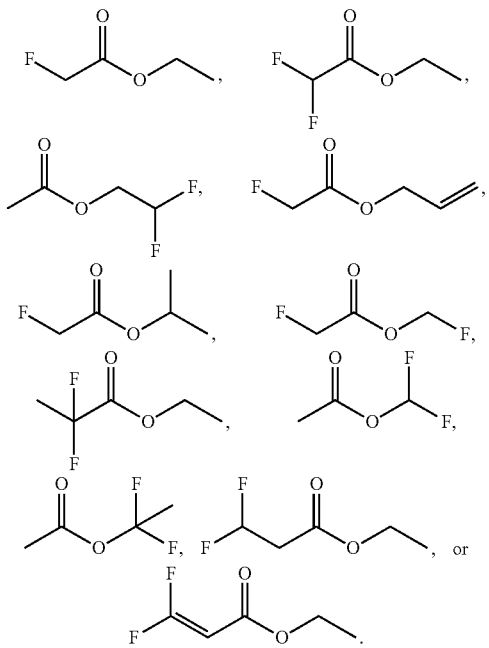

In another aspect, the present invention provides an electronic apparatus including any one of the electrochemical apparatus described above.

Additional aspects and advantages of the embodiments of this application will be partially described in the later description, or explained through implementation of the embodiments of the application.

BRIEF DESCRIPTION OF DRAWINGS

FIG. 1 shows an electron micrograph of a positive active material according to an embodiment of this application.

DESCRIPTION OF EMBODIMENTS

Embodiments of this application will be described in detail below. The embodiments of this application shall not be construed as limitations on the protection scope claimed by this application. Unless otherwise specified, the following terms used herein have the meanings indicated below.

The term "about" used herein are intended to describe and represent small variations. When used in combination with an event or a circumstance, the term may refer to an example in which the exact event or circumstance occurs or an example in which an extremely similar event or circumstance occurs. For example, when used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. In addition, quantities, ratios, and other values are sometimes presented in the format of ranges in this specification. It should be understood that such range formats are used for convenience and simplicity and should be flexibly understood as including not only values clearly designated as falling within the range but also all individual values or sub-ranges covered by the range as if each value and sub-range were clearly designated.

In the description of embodiments and claims, a list of items preceded by the term "one of" may mean any one of the listed items. For example, if items A and B are listed, the phrase "one of A and B" means only A or only B. In another example, if items A, B, and C are listed, the phrase "one of A, B, and C" means only A, only B, or only C. The item A may contain a single element or a plurality of elements. The item B may contain a single element or a plurality of elements. The item C may contain a single element or a plurality of elements.

In the description of embodiments and claims, a list of items preceded by the terms such as "at least one of", "at least one type of" or other similar terms may mean any combination of the listed items. For example, if items A and B are listed, the phrase "at least one of A and B" or "at least one of A or B" means only A, only B, or A and B. In another example, if items A, B, and C are listed, the phrase "at least one of A, B, and C" or "at least one of A, B, or C" means only A, only B, only C, A and B (excluding C), A and C (excluding B), B and C (excluding A), or all of A, B, and C. The item A may contain a single element or a plurality of elements. The item B may contain a single element or a plurality of elements. The item C may contain a single element or a plurality of elements.

In the description of embodiments and claims, the carbon number, namely, the number after the capital letter "C", for example, "1", "3" or "10" in "$C_1$-$C_{10}$" and "$C_3$-$C_{10}$", represents the number of carbon atoms in a specific functional group. That is, the functional groups may include 1-10 carbon atoms and 3-10 carbon atoms, respectively. For example, "$C_1$-$C_4$ alkyl group" or "$C_{1-4}$ alkyl group" refers to an alkyl group having 1 to 4 carbon atoms, for example, CH$_3$—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH (CH$_3$)— or (CH$_3$)$_3$C—.

As used herein, the term "alkyl group" is intended to be a linear saturated hydrocarbon structure having 1 to 10 carbon atoms. The term "alkyl group" is also intended to be a branched or cyclic hydrocarbon structure having 3 to 10 carbon atoms. For example, the alkyl group may be an alkyl group having 1 to 10 carbon atoms, an alkyl group having 1 to 8 carbon atoms, an alkyl group having 1 to 6 carbon atoms, or an alkyl group of 1 to 4 carbon atoms. References to an alkyl group with a specific carbon number are intended to cover all geometric isomers with the specific carbon number. Therefore, for example, "butyl" is meant to include n-butyl, sec-butyl, isobutyl, tert-butyl, and cyclobutyl; and "propyl" includes n-propyl, isopropyl, and cyclopropyl. Examples of alkyl groups include, but are not limited to, methyl, ethyl, n-propyl, isopropyl, cyclopropyl, n-butyl, isobutyl, sec-butyl, tert-butyl, cyclobutyl, n-pentyl, isopentyl, neopentyl, cyclopentyl, methylcyclopentyl, ethylcyclopentyl, n-hexyl, isohexyl, cyclohexyl, n-heptyl, octyl, cyclopropyl, cyclobutyl, norbornyl, and the like. In addition, the alkyl group may be arbitrarily substituted.

The term "alkenyl group" refers to a straight-chain or branched monovalent unsaturated hydrocarbon group having at least one and usually 1, 2, or 3 carbon-carbon double bonds. Unless otherwise defined, the alkenyl group generally contains 2 to 10 carbon atoms. For example, the alkenyl group may be an alkenyl group having 2 to 8 carbon atoms, an alkenyl group having 2 to 6 carbon atoms, or an alkenyl group having 2 to 4 carbon atoms. Representative alkenyl groups include, for example, vinyl, n-propenyl, isopropenyl, n-but-2-enyl, but-3-enyl, and n-hex-3-enyl. In addition, the alkenyl group may be arbitrarily substituted.

The term "alkynyl group" refers to a straight-chain or branched monovalent unsaturated hydrocarbon group having at least one and usually 1, 2, or 3 carbon-carbon triple bonds. Unless otherwise defined, the alkynyl group generally contains 2 to 10 carbon atoms, 2 to 8 carbon atoms, 2 to 6 carbon atoms, or 2 to 4 carbon atoms. Representative alkynyl groups include, for example, ethynyl, prop-2-ynyl (n-propynyl), n-but-2-ynyl and n-hex-3-ynyl. In addition, the alkynyl group may be arbitrarily substituted.

The term "aryl group" covers both monocyclic and polycyclic systems. A polycyclic ring may have two or more rings in which two carbons are shared by two adjacent rings (the rings are "fused"), where at least one of the rings is aromatic, and other rings, for example, may be cycloalkyl, cycloalkenyl, aryl, heterocyclic and/or heteroaryl. For example, the aryl group may contain an aryl group having 6 to 12 carbon atoms or 6 to 10 carbon atoms. Representative aryl groups include, for example, phenyl, methylphenyl, propylphenyl, isopropylphenyl, benzyl and naphth-1-yl, naphth-2-yl, and the like. In addition, the aryl group may be arbitrarily substituted.

When the foregoing substituents are substituted, unless otherwise specified, they are substituted with one or more halogen atoms.

As used herein, the term "halogen" covers F, Cl, Br and I, and is preferably F or Cl.

The term "roundness" or "sphericity" refers to the extent to which a cross-section of a particle approaches a theoretical circle. The roundness $R=(4\pi \times area)/(perimeter \times perimeter)$, when $R=1$, the graph is a circle; and a smaller R means a more irregular graph, and a greater gap between to a circle. In this application, a roundness meter is used to measure the roundness of the positive active material particles. For a specific test method, refer to the following specific examples.

The term "broken particles" means particles with cracks which refer to continuous lines with a length of greater than or equal to 0.1 microns and a width of greater than or equal to 0.01 microns in a cross section of the particles in an image under a scanning electron microscope.

The term "positive active material" refers to a material that can reversibly intercalate and deintercalate lithium ions. In some embodiments of this application, the positive active material includes, but is not limited to, lithium-containing transition metal oxides.

There are two ways to improve the energy density of lithium-ion batteries. One is to use a negative electrode material with a lithiation voltage platform close to that of a graphite negative electrode, but a gram capacity significantly higher than that of a graphite negative electrode, for example, Si/C composite material or SiO$_x$/C composite material. The other is to develop a positive-electrode material with higher specific energy, including lithium-rich manganese-based positive-electrode materials (for example, xLi$_2$MnO$_3$ and (1-x)LiMO$_2$, where 0<x<1, and M is one or more of Ni, Co, Mn, Fe, Ru or Sn), high-nickel positive-electrode materials (for example, LiNi$_x$Co$_y$Mn$_z$O$_2$ (NCM), where 0.5≤x<1, 0<y≤0.2 and 0<z≤0.3), and the like. The spherical secondary particle nickel-rich ternary positive-electrode material (LiNi$_x$Co$_y$Mn$_z$O$_2$ (NCM), where 0.5≤x<1, 0<y≤0.2, and 0<z≤0.3) has been widely used in high energy density lithium-ion batteries due to its good particle fluidity, high tap density, and high mass specific energy. However, the inventors of this application have found that during high-voltage charging of a spherical secondary particle nickel-rich ternary, delithiation capacity is up to more than 80%, and the material lattice shrinks anisotropically, resulting in a sharp increase in the internal stress of the particles. Secondary particles are broken during repeated cycles, and physical contact between primary particles is severely damaged, resulting in a sharp increase in the charge transfer impedance of the battery and a rapid decay of the capacity at the late stage of cycling. In addition, after the secondary particles are broken, the electrolyte quickly penetrates into the interior of the secondary particles, and has many side reactions with the primary particles, resulting in swelling and other safety problems in cycling of the battery, especially during high-temperature cycling. In order to improve the cycle performance of the nickel-rich material battery system and suppress gas generation during cycles, in the present invention, for example, a grain boundary modification is performed for the spherical secondary particle nickel-rich NCM positive electrode to inhibit particle breakage, combined with the addition of appropriate protective additives (such as a compound of Formula I and LiPO$_2$F$_2$), or for example, a mixture of primary particles and secondary particles is used to improve particle breakage, combined with the addition of appropriate protective additives (such as a compound of Formula I and LiPO$_2$F$_2$). These combinations can significantly improve the high-temperature storage performance and high-temperature cycle performance and suppress gas generation during high-temperature cycles.

I. ELECTROCHEMICAL APPARATUS

The electrochemical apparatus according to this application includes any apparatus in which electrochemical reactions take place. Specific examples of the apparatus include all kinds of primary batteries, secondary batteries, fuel batteries, solar batteries, or capacitors. Especially, the electrochemical apparatus is a lithium secondary battery, including lithium metal secondary batteries, lithium-ion secondary batteries, lithium polymer secondary batteries, or lithium-ion polymer secondary batteries. In some embodiments, the electrochemical apparatus of this application includes a positive electrode, a negative electrode, a separator, and an electrolyte.

Positive Electrode

In some embodiments, the positive electrode includes a current collector and a positive active material layer provided on the current collector, and the positive active material layer contains a positive active material.

The positive active material includes at least one lithium intercalation compound that reversibly intercalates and deintercalates lithium ions. In some embodiments of this application, the positive active material includes a lithium-containing transition metal oxide. In some embodiments, the positive active material includes a composite oxide. In some embodiments, the composite oxide contains lithium and at least one element selected from cobalt, manganese and nickel.

In some embodiments, the positive active material layer includes a phosphorus-containing compound, and the phosphorus-containing compound includes at least one of $Li_3PO_4$ or $LiMPO_4$, where M is selected from at least one of Co, Mn, or Fe.

In some embodiments, the phosphorous-containing compound is contained in a surface or a grain boundary of the positive active material.

In some embodiments, the positive active material includes $LiNi_xCo_yMn_zO_2$, where $0.55<x<0.92$, $0.03<y<0.2$, and $0.04<z<0.3$.

In some embodiments, the positive active material includes an element Q, and the Q is selected from at least one of Zr, Ti, Yr, V, Al, Mg, or Sn.

The inventors have found through research that a main function of nickel is to increase energy density in the positive active material containing a nickel ternary material. In the same charge and discharge voltage range, a higher nickel content means a higher gram capacity. However, in practical use of high-nickel materials in electrochemical apparatuses, due to the high delithiation capacity and the large expansion and contraction of cell volume under the same voltage, the particles are easily broken and easily have side reactions with the electrolyte. After the particles are broken, a new interface will be exposed, causing the electrolyte to penetrate into the particles through the cracks and have side reactions with the positive active material at the new interface, which will aggravate gas generation and cause that the capacity of the electrochemical apparatus decays rapidly as the charge-discharge cycles progress. In addition, during the charging process of the electrochemical apparatus, as lithium ions continuously deintercalate from the positive active material, a binding force between an active metal (for example, nickel) in the positive active material and oxygen is weakened, and oxygen release occurs. The released oxygen will oxidize the electrolyte and increase gas generation. The above-mentioned problems severely limit the utilization of high-nickel materials in high energy-density electrochemical apparatuses (especially in the positive active material $LiNi_xCo_yMn_zO_2$, where $x \geq 0.6$).

First particles are a collection of numerous single crystal particles, where a single crystal is a crystal in which the particles inside are regularly and periodically arranged in a three-dimensional space. The morphology of the first particles is spherical or ellipsoidal, with a large roundness and a large cross-sectional area. Second particles are a collection of single crystals with a larger grain size.

In some embodiments, the positive active material layer includes first particles, and a roundness of the first particles is 0.4 to 1, and with respect to a cross-sectional area of the positive electrode perpendicular to the current collector, a cross-sectional area of the first particle is greater than or equal to 20 square microns, and a sum of the cross-sectional areas of the first particles is 5% to 50% of the cross-sectional area of positive electrode.

In some embodiments, a specific surface area (BET) of the first particles is about 0.14 $m^2/g$ to about 0.95 $m^2/g$;

In some embodiments, Dv50 of the first particles is about 5.5 microns to about 14.5 microns. Dv90 is less than or equal to 18 microns.

In some embodiments, the positive active material layer includes second particles, and a roundness of the second particles is less than 0.4, and with respect to the cross-sectional area of the positive electrode perpendicular to the current collector, a cross-sectional area of the second particle is less than the cross-sectional area of the first particle.

In some embodiments, with respect to the cross-sectional area of the positive electrode perpendicular to the current collector, a sum of the cross-sectional areas of the second particles is 5% to 60% of the cross-sectional area of positive electrode.

In some embodiments, a porosity of the positive electrode is ≤25%.

In some embodiments, with respect to the cross-sectional area of the positive electrode perpendicular to the current collector, a cross-sectional area of the positive current collector takes up a proportion of 5% to 20%.

In some embodiments, a compacted density of the positive active material layer is less than or equal to 3.6 $g/cm^3$.

In some embodiments, the positive active material includes a $Li_3PO_4$ modified nickel-rich positive-electrode material or consists of a $Li_3PO_4$ modified nickel-rich positive-electrode material, and its preparation method can be exemplified by the following two methods.

Liquid-phase mixing method: the positive-electrode material ($LiNi_{0.84}Co_{0.13}Mn_{0.06}O_2$) and $H_3PO_4$ are dispersed in an ethanol solution, magnetically stirred for 60 minutes, and then transferred to an oil bath at 80° C. and stirred until ethanol is completely evaporated to obtain the $Li_3PO_4$ modified ternary positive active material. Then the material is crushed and sieved to obtain positive active materials with different particle sizes, so that the obtained $Li_3PO_4$ content accounts for about 1 wt % of the total weight of the modified nickel-rich ternary positive-electrode material.

Sol-gel method: the positive-electrode material ($LiNi_{0.84}Co_{0.13}Mn_{0.06}O_2$) is added to an ethanol solution containing lithium nitrate, citric acid and phosphoric acid, and stirred vigorously, with a mass ratio of the positive-electrode material to $Li_3PO_4$ kept at 99:1. Then it is heated to 80° C. and stirred until the solvent is evaporated completely. Finally, it is calcined in an air atmosphere at 600° C. for 2 hours to obtain the $Li_3PO_4$ modified positive-electrode material.

In some embodiments, the positive active material includes a $LiMPO_4$ modified nickel-rich positive-electrode material or consists of a $Li_3MO_4$ modified nickel-rich positive-electrode material, and its preparation method is similar to that of the $Li_3PO_4$ modified nickel-rich positive-electrode material.

In some embodiments, the positive active material may have a coating on its surface, or may be mixed with another compound having a coating. The coating may include at least one compound of a coating element selected from oxides of the coating element, hydroxides of the coating element, hydroxyl oxides of the coating element, oxycarbonates of the coating element, and hydroxy carbonates of the coating element. The compound used for coating may be amorphous or crystalline.

In some embodiments, the coating element contained in the coating may include Mg, Al, Co, K, Na, Ca, Si, Ti, V, Sn, Ge, Ga, B, As, Zr or any combination thereof. The coating can be applied by any method as long as the method does not adversely affect the performance of the positive active material. For example, the method may include any coating method known in the art, for example, spraying and dipping.

The positive active material layer further includes a binder, and optionally, further includes a conductive material. The binder enhances binding between particles of the positive active material, and binding between the positive active material and the current collector.

In some embodiments, the binder includes, but is not limited to: polyvinyl alcohol, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(vinylidene fluoride), polyethylene, polypropylene, styrene-butadiene rubber, acrylic styrene-butadiene rubber, epoxy resin, nylon, and the like.

In some embodiments, the conductive material includes, but is not limited to: a carbon-based material, a metal-based material, a conductive polymer or any mixture thereof. In some embodiments, the carbon-based material is selected from natural graphite, artificial graphite, carbon black, acetylene black, Ketjen black, carbon fiber, or any combination thereof. In some embodiments, the metal-based material is selected from metal powder, metal fiber, copper, nickel, aluminum or silver. In some embodiments, the conductive polymer is a polyphenylene derivative.

In some embodiments, the current collector may be, but is not limited to, aluminum (Al).

The positive electrode can be prepared by a preparation method known in the art. For example, the positive electrode may be obtained by mixing an active material, a conductive material, and a binder in a solvent to prepare an active material composition, and applying the active material composition on the current collector as a coating. In some embodiments, the solvent may include, but is not limited to, N-methylpyrrolidone and the like.

In some embodiments, the positive electrode is made by forming, on the current collector, a positive-electrode material using a positive active material layer including lithium transition metal-based compound powder and a binder.

In some embodiments, the positive active material layer can usually be made by the following operations: dry mixing the positive-electrode material and the binder (a conductive material and a thickener as required) to form a sheet, pressing the obtained sheet to the positive current collector, or dissolving or dispersing these materials in a liquid medium to form a slurry, which is applied on the positive current collector as a coating and dried.

Negative Electrode

The material, composition, and manufacturing method of the negative electrode used in the electrochemical apparatus of this application may include any technology disclosed in the prior art. In some embodiments, the negative electrode is the negative electrode described in U.S. Pat. No. 9,812,739B, which is hereby incorporated by reference in its entirety.

In some embodiments, the negative electrode includes a current collector and a negative active material layer on the current collector. The negative active material includes a material that reversibly intercalates/deintercalates lithium ions. In some embodiments, the material that reversibly intercalates/deintercalates lithium ions includes a carbon material. In some embodiments, the carbon material may be any carbon-based negative active material commonly used in lithium-ion rechargeable batteries. In some embodiments, the carbon material includes, but is not limited to: crystalline carbon, amorphous carbon, and combinations thereof. The crystalline carbon may be amorphous, plate-shaped, flake-shaped, spherical or fiber-shaped natural graphite or artificial graphite. The amorphous carbon may be soft carbon, hard carbon, a mesophase pitch carbonization product, burnt coke, or the like.

In some embodiments, the negative electrode includes a negative active material layer. The specific types of the negative active material are not subject to specific restrictions, and can be selected according to requirements. In some embodiments, the negative active material includes, but is not limited to: lithium metal, structured lithium metal, natural graphite, artificial graphite, mesocarbon microbeads (MCMB), hard carbon, soft carbon, silicon, a silicon-carbon composite, a Li—Sn alloy, a Li—Sn—O alloy, Sn, SnO, $SnO_2$, spinel structure lithiated $TiO_2$—$Li_4Ti_5O_{12}$, a Li—Al alloy or any combination thereof. The silicon-carbon composite refers to a composite containing at least about 5 wt % silicon based on a weight of the silicon-carbon negative active material.

When the negative electrode includes a silicon-carbon compound, based on the total weight of the negative active material, silicon:carbon is about 1:10 to 10:1, and a median particle size D50 of the silicon-carbon compound is about 0.1 to 20 microns. When the negative electrode includes an alloy material, the negative active material layer can be formed using methods such as vapor deposition method, sputtering method, and plating method. When the negative electrode includes lithium metal, the negative active material layer is formed of, for example, a conductive skeleton having a spherical stranded shape and metal particles dispersed in the conductive skeleton. In some embodiments, the spherical stranded conductive skeleton may have a porosity of about 5% to about 85%. In some embodiments, the lithium metal negative active material layer may be further provided with a protective layer.

In some embodiments, the negative active material layer may include a binder, and optionally, further includes a conductive material. The binder improves the binding of the negative active material particles with each other and the binding of the negative active material with the current collector. In some embodiments, the binder includes, but is not limited to: polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(vinylidene fluoride), polyethylene, polypropylene, styrene-butadiene rubber, acrylic styrene-butadiene rubber, epoxy resin, and nylon.

In some embodiments, the conductive material includes, but is not limited to: a carbon-based material, a metal-based material, a conductive polymer or any mixture thereof. In some embodiments, the carbon-based material is selected from natural graphite, artificial graphite, carbon black, acetylene black, Ketjen black, carbon fiber, or any combination thereof. In some embodiments, the metal-based material is selected from metal powder, metal fiber, copper, nickel, aluminum or silver. In some embodiments, the conductive polymer is a polyphenylene derivative.

In some embodiments, the current collector includes, but is not limited to: copper foil, nickel foil, stainless steel foil, titanium foil, nickel foam, copper foam, a polymer substrate coated with a conductive metal, and any combination thereof.

The negative electrode can be prepared by using a preparation method known in the art. For example, the negative electrode may be obtained by using the following method: mixing an active material, a conductive material, and a binder in a solvent to prepare an active material composition, and applying the active material composition on a current collector as a coating. In some embodiments, the solvent may include, but is not limited to, water and the like.

Separator

In some embodiments, the electrochemical apparatus according to this application has a separator provided between the positive electrode and the negative electrode to prevent short circuits. The separator used in the electrochemical apparatus according to this application is not particularly limited to any material or shape, and may be based on any technology disclosed in the prior art. In some embodiments, the separator includes a polymer or an inorganic substance formed by a material stable to the electrolyte of this application.

For example, the separator may include a substrate layer and a surface treatment layer. The substrate layer is a non-woven fabric, membrane, or composite membrane having a porous structure, and a material of the substrate layer is selected from at least one of polyethylene, polypropylene, polyethylene terephthalate, and polyimide. Specifically, a polypropylene porous membrane, a polyethylene porous membrane, polypropylene nonwoven fabric, polyethylene nonwoven fabric, or polypropylene-polyethylene-polypropylene porous composite membrane can be selected. The substrate material layer can have one layer or multiple layers. When the substrate material layer has multiple layers, the polymer composition of different substrate material layers can be the same or different, and the weight average molecular weight of polymers of different substrate material layers is not all the same. When the substrate layer has multiple layers, closed cell temperatures of polymers of different substrate layers are different.

In some embodiments, at least one surface of the substrate layer is provided with a surface treatment layer, and the surface treatment layer may be a polymer layer or an inorganic substance layer, or a layer formed by mixing a polymer and an inorganic sub stance.

In some embodiments, the separator includes a porous substrate and a coating layer, and the coating layer includes inorganic particles and a binder.

In some embodiments, the coating layer has a thickness of about 0.5 microns to about 10 microns, about 1 microns to about 8 microns, or about 3 microns to about 5 microns.

In some embodiments, the inorganic particles are selected from at least one of $SiO_2$, $Al_2O_3$, CaO, $TiO_2$, $ZnO_2$, MgO, $ZrO_2$, $SnO_2$, $Al(OH)_3$ or A100H. In some embodiments, a particle size of the inorganic particles is about 0.001 microns to about 3 microns.

In some embodiments, the binder is selected from at least one of polyvinylidene fluoride (PVDF), polyvinylidene fluoride-hexafluoroethylene copolymer (PVDF-HFP), polyvinylpyrrolidone (PVP), polyacrylate, pure acrylic emulsion (an anionic acrylic emulsion obtained by copolymerization of acrylate and special functional monomers), styrene-acrylic emulsion ((styrene-acrylate emulsion) obtained by emulsion copolymerization of styrene and acrylic ester monomers) and styrene-butadiene emulsion (SBR, obtained by emulsion copolymerization of butadiene and styrene).

Electrolyte

The electrochemical apparatus according to some embodiments of the present invention includes a positive electrode, a negative electrode, a separator and an electrolyte, where the positive electrode includes a current collector and a positive active material layer, and the positive active material layer includes a positive active material; and the electrolyte includes a compound of Formula I:

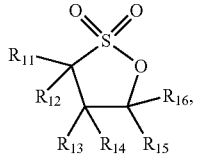

Formula I where $R_{11}$, $R_{12}$, $R_{13}$, $R_{14}$, $R_{15}$ and $R_{16}$ are each independently selected from: H, halogen, and the following substituted or unsubstituted groups: a $C_{1-8}$ alkyl group, a $C_{2-8}$ alkenyl group, a $C_{2-8}$ alkynyl group, or a $C_{6-12}$ aryl group; and an amount of the compound of Formula I per 1 g of the positive active material is about 0.001 g to about 0.064 g.

In some embodiments, $R_{11}$, $R_{12}$, $R_{13}$, $R_{14}$, $R_{15}$ and $R_{16}$ are each independently selected from: H, halogen, and the following substituted or unsubstituted groups: a $C_{1-6}$ alkyl group or $C_{1-4}$ alkyl group, a $C_{2-6}$ alkenyl group or $C_{2-4}$ alkenyl group, a $C_{2-6}$ alkynyl group or $C_{2-4}$ alkynyl group, or a $C_{6-10}$ aryl group.

In some embodiments, $R_{11}$, $R_{12}$, $R_{13}$, $R_{14}$, $R_{15}$ and $R_{16}$ are each independently selected from: H, F, methyl, ethyl, propyl, isopropyl, vinyl, or $-CF_3$.

In some embodiments, about 0.01 g to about 0.06 g of the compound of Formula I is required per 1 g of the positive active material; and in some embodiments, about 0.015 g, about 0.02 g, about 0.025 g, about 0.03 g, about 0.035 g, about 0.04 g, about 0.045 g, about 0.05 g, or about 0.055 g of the compound of Formula I is required per 1 g of the positive active material.

The inventors have found through research that the positive-electrode material is subject to particle breakage in the late stage of cycling, and the compound of Formula I has good thermal stability, moderate reaction rate, and can be continuously and slowly consumed during cycling, forming an effective protective layer on the surface of the material after the material particles are broken, so as to slow down gas generation caused by side reactions.

The inventors have also found through research that film-forming impedance of the compound of Formula I is relatively large. Combined with the P element modification on the surface of the positive-electrode material, it can not only improve stability of the material itself and ion conduction, but also reduce reactions of the compound of Formula I in the early stage of cycling and reduce initial impedance, while ensuring a film-forming effect in the late stage of cycling, so as to further improve the cycle performance and reduce gas generation.

In some embodiments, the compound of Formula I includes at least one of the following compounds:

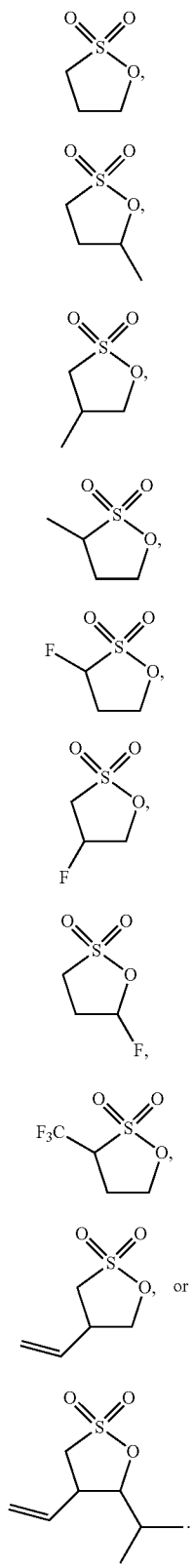

Compound I-1

Compound I-2

Compound I-3

Compound I-4

Compound I-5

Compound I-6

Compound I-7

Compound I-8

Compound I-9 or

Compound I-10

In some embodiments, the electrolyte further includes an additive A, and the additive A includes at least one of $LiBF_4$, $LiPO_2F_2$, LiFSI, LiTFSI, 4,5-dicyano-2-trifluoromethylimidazolium, lithium difluoro bis (oxalate) phosphate, lithium difluoroacetate borate, or lithium bisoxalate borate; and an amount of the additive A is about 0.000026 g to about 0.019 g per 1 g of the positive active material.

The inventors have found through research that the additive A can preferentially form a film on the surface of the positive-electrode material so as to form an interface film with relatively low impedance, reduce side reactions of the electrolyte on the surface of the positive-electrode material, and reduce reactions of the compound of Formula I in the early stage of cycling, thereby ensuring the stability in the early stage of cycling, and improving cycle performance and reducing gas generation.

In some embodiments, the additive A includes lithium difluorophosphate ($LiPO_2F_2$).

In some embodiments, an amount of the additive A is about 0.00003 g to 0.015 g per 1 g of the positive active material. In some embodiments, the amount of the additive A is about 0.00006 g, about 0.00008 g, about 0.0001 g, about 0.0003 g, about 0.0005 g, about 0.0007 g, about 0.001 g, about 0.003 g, about 0.005 g, about 0.007 g, about 0.01 g, about 0.013 g, about 0.015 g, or about 0.017 g per 1 g of the positive active material.

In some embodiments, the electrolyte further includes an additive B, and the additive B includes vinylene carbonate (VC), fluoroethylene carbonate (FEC), ethylene sulfate (DTD), tris(trimethylsilyl) phosphate (TMSP), tris(trimethylsilyl) borate (TMSB), adiponitrile (ADN), succinonitrile (SN), 1, 3, 5-pentanetricarbonitrile, 1, 3, 6-hexanetricarbonitrile (HTCN), 1, 2, 6-hexanetricarbonitrile, or 1, 2, 3-tris (2-cyanoethoxy)propane (TECP).

In some embodiments, a mass ratio of the compound of Formula I to the additive B is 7:1 to 1:7.

In some embodiments, an amount of the additive B is 0.0001 g to 0.2 g of the additive B is required per 1 g of the positive active material.

In some embodiments, the mass ratio of the compound of Formula I to the additive B is about 7:1, about 6:1, about 5:1, about 4:1, about 3:1, about 2:1, about 1:1, about 1:2, about 1:3, about 1:4, about 1:5, about 1:6, or about 1:7.

In some embodiments, an amount of the additive B is 0.0005 g to 0.18 g per 1 g of the positive active material. In some embodiments, the amount of the additive B is about 0.0005 g, about 0.001 g, about 0.005 g, about 0.01 g, about 0.03 g, about 0.05 g, about 0.07 g, about 0.1 g, about 0.12 g, about 0.15 g or about 0.18 g per 1 g of the positive active material.

The inventors have found through research that the additive B can form a film on the positive electrode, adjust composition of the positive-electrode film, and relatively increase organic layer content, thus enhancing stability of the positive-electrode film formation and further improve the cycle stability.

In some embodiments, the electrolyte further includes a compound of Formula II:

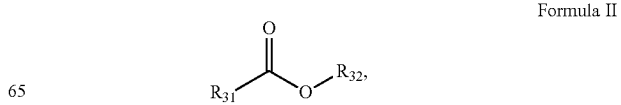

Formula II where $R_{31}$ and $R_{32}$ are each independently selected from a substituted or unsubstituted $C_{1-10}$ alkyl group, or a substituted or unsubstituted $C_{2-8}$ alkenyl group, where being substituted refers to substitution with one or more halogen atoms; and based on a total weight of the electrolyte, a content of the compound of Formula II is 0.5 wt % to 50 wt %.

In some embodiments, $R_{31}$ and $R_{32}$ are each independently selected from the following substituted or unsubstituted groups: a $C_{1-8}$ alkyl group, a $C_{1-6}$ alkyl group, a $C_{1-4}$ alkyl group, a $C_{2-6}$ alkenyl group, or a $C_{2-4}$ alkenyl group, where being substituted refers to substitution with one or more halogen atoms.

In some embodiments, at least one of $R_{31}$ and $R_{32}$ is substituted with one or more halogen atoms.

In some embodiments, $R_{31}$ and $R_{32}$ are each independently selected from the following groups that are unsubstituted or substituted with one or more F atoms: methyl, ethyl, propyl, isopropyl, vinyl, or propenyl; and in some embodiments, at least one of $R_{31}$ and $R_{32}$ is substituted with one or more F atoms.

In some embodiments, based on the total weight of the electrolyte, the content of the compound of Formula II is about 1 wt % to 45 wt %. In some embodiments, based on the total weight of the electrolyte, the content of the compound of Formula II is about 5 wt %, about 10 wt %, about 15 wt %, about 20 wt %, about 25 wt %, about 25 wt %, about 30 wt %, about 35 wt %, or about 40 wt %.

In some embodiments, the compound of Formula II includes at least one of the following compounds:

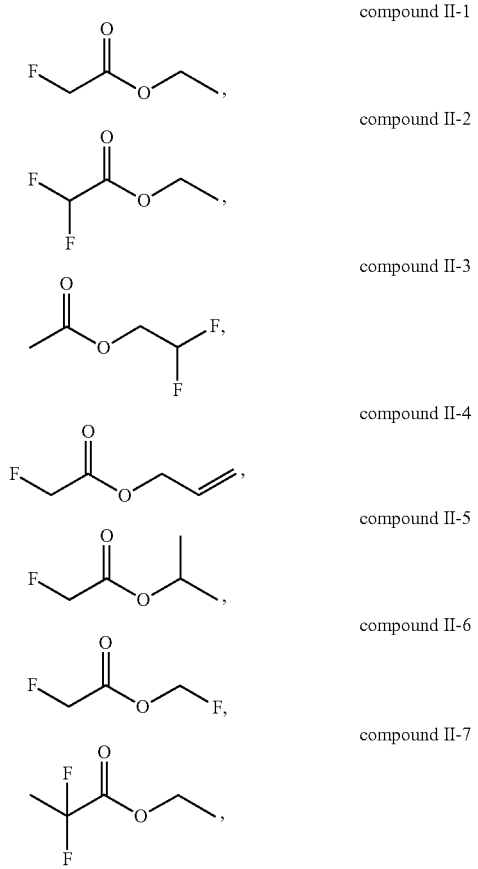

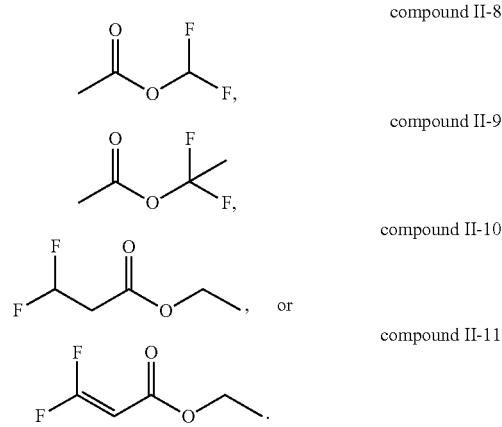

The inventors have found through research that the combination of the compound of Formula I and the compound of Formula II can reduce ion transport resistance, and can form a protective layer on the positive electrode. After particle breakage occurs in the late stage of cycling, the compounds of Formula I and Formula II work together to effectively repair the protective layer on the positive-electrode surface, thereby increasing the cycle life.

In some embodiments, the electrolyte further includes a lithium salt and an organic solvent.

In some embodiments, the lithium salt is selected from one or more of inorganic lithium salts and organic lithium salts. In some embodiments, the lithium salt includes at least one of fluorine, boron or phosphorus. In some embodiments, the lithium salt is selected from one or more of the following lithium salts: lithium hexafluorophosphate $LiPF_6$, lithium bistrifluoromethanesulfonimide $LiN(CF_3SO_2)_2$ (abbreviated as LiTFSI), bis(fluorosulfonyl) Lithium imide $Li(N(SO_2F)_2)$ (abbreviated as LiFSI), lithium hexafluoroarsenate $LiAsF_6$, lithium perchlorate $LiClO_4$, or lithium trifluoromethanesulfonate $LiCF_3SO_3$.

In some embodiments, a concentration of the lithium salt is 0.3 mol/L to 1.5 mol/L. In some embodiments, the concentration of the lithium salt is 0.5 mol/L to 1.3 mol/L or 0.8 mol/L to 1.2 mol/L. In some embodiments, the concentration of the lithium salt is 1.10 mol/L.

The organic solvent includes at least one of ethylene carbonate (EC), propylene carbonate (PC), diethyl carbonate (DEC), ethyl methyl carbonate (EMC), dimethyl carbonate (DMC), sulfolane (SF), γ-butyrolactone (γ-BL), propyl ethyl carbonate, methyl formate (MF), ethyl formate (MA), ethyl acetate (EA), ethyl propionate (EP), propyl propionate (PP), methyl propionate, methyl butyrate, ethyl butyrate, ethyl fluorocarbonate, dimethyl fluorocarbonate, or diethyl fluorocarbonate.

In some embodiments, the solvent accounts for 70 wt % to 95 wt % of the electrolyte.

The electrolyte used in the electrochemical apparatus according to this application is any one of the foregoing electrolytes in this application. In addition, the electrolyte used in the electrochemical apparatus according to this application may also include other electrolytes within the scope without departing from the essence of this application.

II. APPLICATION

The electrochemical apparatus according to this application is not particularly limited to any purpose, and may be used for any known purposes. For example, the electrochemical apparatus may be used for a notebook computer, a pen-input computer, a mobile computer, an electronic book player, a portable telephone, a portable fax machine, a portable copier, a portable printer, a headset, a video recorder, a liquid crystal television, a portable cleaner, a portable CD player, a mini-disc, a transceiver, an electronic notebook, a calculator, a storage card, a portable recorder, a radio, a standby power source, a motor, an automobile, a motorcycle, a motor bicycle, a bicycle, a lighting appliance, a toy, a game console, a clock, an electric tool, a flash lamp, a camera, a large household battery, a lithium ion capacitor, or the like.

III. EXAMPLES

Below, this application will be further specifically described with Examples and Comparative Examples, and this application is not limited to these Examples as long as the essence of this application is not departed from.

1. Preparation of a Lithium-Ion Battery

The preparation processes of the lithium-ion batteries of Comparative Example 1-1, Comparative Example 1-2, and Example 1-1 to Example 1-21 were as follows:

(1) Preparation of a Negative Electrode

Artificial graphite serving as a negative active material, sodium carboxymethyl cellulose (CMC) as a thickener, and styrene butadiene rubber (SBR) as a binder were mixed at a weight ratio of 97:1:2. Deionized water was added. Then, the resulting mixture was stirred by a vacuum mixer to obtain a negative slurry with a solid content of 54 wt %. The negative slurry was applied uniformly on a copper foil negative current collector. The coated copper foil was dried at 85° C., and cold pressed to obtain a negative active material layer. Then, after cutting and slitting, the negative active material layer was dried under vacuum at 120° C. for 12 hours to obtain a negative electrode.

(2) Preparation of a positive electrode

A $Li_3PO_4$ modified positive active material was prepared by using a liquid-phase mixing method. 99 g $LiNi_{0.84}Co_{0.13}Mn_{0.06}O_2$ and 1 g $H_3PO_4$ were ultrasonic-processed for 10 minutes and dispersed in an ethanol solution, magnetically stirred for 60 minutes, and then transferred to an oil bath at 80° C. and stirred until ethanol is completely evaporated to obtain a $Li_3PO_4$ modified ternary positive active material. Then, the material was crushed and sieved to obtain positive active materials with different particle sizes.

The $Li_3PO_4$ modified positive active material $LiNi_{0.84}Co_{0.13}Mn_{0.06}O_2$ (with a specific surface area of 0.45 m$^3$/g), Super P as a conductive agent, and polyvinylidene fluoride as a binder were mixed at weight ratio of 97:1.4:1.6. N-methylpyrrolidone (NMP) was added. Then the mixture was stirred by a vacuum mixer to obtain a positive slurry with a solid content of 72 wt %. The positive slurry was applied uniformly on an aluminum foil positive current collector. Then the coated aluminum foil was dried at 85° C., followed by cold pressing, cutting and slitting. Then, it was dried under vacuum at 85° C. for 4 hours to obtain a positive electrode. The positive electrode included a positive active material layer, and the positive active material layer included a positive active material; with respect to a cross-sectional area of the positive electrode perpendicular to the aluminum foil, a sum of cross-sectional areas of first particles in the positive electrode accounted for 27.1% of the cross-sectional area, and a sum of cross-sectional areas of second particles in the positive electrode accounted for 37.8% of the cross-sectional area. A compacted density of the positive active material layer was 3.4 g/cm$^3$.

The method to obtain the compacted density was as follows: performing cutting to obtain an electrode plate with a diameter of 18 mm, measuring thickness of the plate with a ten-meter ruler, and weighing mass of the plate. Compacted density=(mass of the plate−mass of the current collector in the plate)/(area of the plate×(thickness of the plate−thickness of the current collector)).

(3) Preparation of an electrolyte

In a glove box under a dry argon atmosphere, ethylene carbonate (EC), propylene carbonate (PC), ethyl methyl carbonate (EMC), and diethyl carbonate (DEC) were mixed at a mass ratio of EC:PC:EMC:DEC=20:10:30:40. An additive was then added and dissolved, and the mixture was thoroughly stirred. Then, a lithium salt $LiPF_6$ was added and mixed uniformly to obtain an electrolyte with a concentration of $LiPF_6$ being 1.10 mol/L. The specific types and amounts of additives used in the electrolyte are shown in Table 1. In Table 1, the amounts of additives were calculated based on the gram weight required per 1 g of the modified positive active material.

(4) Preparation of a separator

A polyethylene (PE) separator with a thickness of 9 microns was used, which was coated with a polyvinylidene fluoride (PVDF) slurry and an $Al_2O_3$ slurry, and dried to obtain a final separator.

(5) Preparation of a lithium-ion battery

The positive electrode, separator, and negative electrode were stacked in order, so that the separator is placed between the positive electrode plate and the negative electrode plate for separation. Then they were wound with tabs welded thereto and placed in an outer packaging aluminum foil film. Then the above prepared electrolyte was injected, followed by processes such as vacuum packaging, standing, chemical conversion, shaping and capacity testing, to obtain a soft-packed lithium-ion battery (with a thickness of 3.3 mm, a width of 39 mm and a length of 96 mm).

Example 1-22: the electrolyte of the lithium-ion battery was prepared according to the following method, and the other processes for preparing the lithium-ion battery were exactly the same as those of comparative example 1-1.

In a glove box under a dry argon atmosphere, ethylene carbonate (EC), propylene carbonate (PC), ethyl methyl carbonate (EMC), diethyl carbonate (DEC) and a Compound II-3 were mixed at a mass ratio of EC:PC:EMC:DEC:Compound II-3=20:10:40:20:10. Then an additive was added and dissolved. The resulting mixture was stirred thoroughly, and then a lithium salt $LiPF_6$ was added, followed by mixing uniformly to obtain an electrolyte, with a concentration of $LiPF_6$ being 1.10 mol/L. The specific types and amounts of additives used in the electrolyte are shown in Table 1. In Table 1, the amounts of additives were the gram weight required per 1 g of the modified positive active material.

Example 1-23: The electrolyte of the lithium-ion battery was prepared according to the following method, and the other processes for preparing the lithium-ion battery were exactly the same as those of Comparative Example 1-1.

In a glove box under a dry argon atmosphere, ethylene carbonate (EC), propylene carbonate (PC), ethyl methyl carbonate (EMC), diethyl carbonate (DEC) and a Compound II-3 were mixed at a mass ratio of EC:PC:EMC:DEC:Compound II-3=20:10:20:20:30. Then an additive was added and dissolved. The resulting mixture was stirred thoroughly, and then a lithium salt $LiPF_6$ was added, followed by mixing uniformly to obtain an electrolyte with a concentration of $LiPF_6$ being 1.10 mol/L. The specific types and amounts of additives used in the electrolyte are shown in Table 1. In Table 1, the amounts of additives were the gram weight required per 1 g of the modified positive active material.

Example 1-24: The electrolyte of the lithium-ion battery was prepared according to the following method, and the other processes for preparing the lithium-ion battery were exactly the same as those of Comparative Example 1-1.

In a glove box under a dry argon atmosphere, ethylene carbonate (EC), propylene carbonate (PC), ethyl methyl carbonate (EMC), diethyl carbonate (DEC) and a Compound II-2 were mixed at a mass ratio of EC:PC:EMC:DEC: Compound II-2=20:10:30:30:10. Then an additive was added and dissolved. The resulting mixture was stirred thoroughly, and then a lithium salt $LiPF_6$ was added, followed by mixing uniformly to obtain an electrolyte with a concentration of $LiPF_6$ being 1.10 mol/L. The specific types and amounts of additives used in the electrolyte are shown in Table 1. In Table 1, the amounts of additives were the gram weight required per 1 g of the positive active material.

Example 1-25: The positive electrode of the lithium-ion battery was prepared according to the following method, and the other processes for preparing the lithium-ion battery were exactly the same as those of Comparative Example 1-1.

An $Li_3PO_4$ modified positive-electrode material was prepared by using a sol-gel method. 91.7 g positive-electrode material (molecular formula $LiNi_{0.84}Co_{0.13}Mn_{0.06}O_2$) was added to an ethanol solution containing 2 g lithium nitrate, 5.4 g citric acid and 0.9 g phosphoric acid, and stirred vigorously, with a mass ratio of the positive-electrode material to $Li_3PO_4$ kept at 99:1. Then the resulting solution was heated to 80° C. and continued to be stirred until the solvent was evaporated completely. Finally, it was calcined in an air atmosphere at 600° C. for 2 hours to obtain a $Li_3PO_4$ modified positive-electrode material.

Example 1-26: The preparation process of the lithium-ion battery was exactly the same as that of Example 1-2, except that the compacted density of the positive active material layer was 3.3 g/cm³.

Example 1-27: The preparation process of the lithium-ion battery was exactly the same as that of Example 1-2, except that the compacted density of the positive active material layer was 3.6 g/cm³.

Example 1-28: The preparation process of the lithium-ion battery was exactly the same as that of Example 1-2, except that the ratio of a sum of cross-sectional areas of first particles in the positive active material to the cross-sectional area of the positive active material was 10.4%.

Examples 1-29 to 1-31: The preparation process of the lithium-ion battery was exactly the same as that of Example 1-2, except that the used positive active material $LiNi_{0.84}Co_{0.13}Mn_{0.06}O_2$ was not modified by $Li_3PO_4$.

Example 1-32: The preparation process of the lithium-ion battery was exactly the same as that of Example 1-2, except that the positive active material was $LiNi_{0.84}Co_{0.13}Mn_{0.058}Zr_{0.002}O_2$.

Example 1-33: The preparation process of the lithium-ion battery was exactly the same as that of Example 1-2, except that the positive active material was $LiNi_{0.84}Co_{0.13}Mn_{0.057}Al_{0.001}Zr_{0.002}O_2$.

Comparative Example 1-3: The preparation process of the lithium-ion battery was exactly the same as that of Comparative Example 1-1, except that the used positive active material $LiNi_{0.84}Co_{0.13}Mn_{0.6}O_2$ was not modified by $Li_3PO_4$.

Comparative Examples 2-1 to 2-4 and Examples 2-1 to 2-18: The preparation process of the lithium-ion battery was exactly the same as that of Comparative Example 1-1, except for the type of the positive-electrode material and the electrolyte.

2. Test methods for particle roundness, particle cross-sectional area, and proportion by area (1) Particle Roundness The roundness of particles of the positive active material was tested with a roundness meter of model DTP-550A.

(2) Particle cross-sectional area and proportion by area

The positive electrode was cut in a direction perpendicular to the positive current collector using an ion polisher (model of JEOL-IB-09010CP) to obtain a cross section. The cross section was observed using a scanning electron microscope with appropriate magnification, pictures were taken in the backscattering mode, and the software Image J was used to identify object shapes so as to identify the roundness and cross-sectional areas of particles, thereby finding particles A, broken particles in the particles A, and the current collector, as well as the corresponding areas. A total area of the cross section of the positive electrode plate was S, a total area of the particles A was S1 (including broken particles), a total area of broken particles in the particles A was S2, an area of the positive current collector was S3, a porosity was P, and proportions by area of the conductive agent and the binder were ignored. In this application, the roundness of the particles A was greater than or equal to 0.4, and the cross-sectional area of a single particle A was greater than or equal to 20 square microns.

The proportion of the total area of the particles $A=S_1/S\times 100\%$;

the proportion of the total area of broken particles in the particles $A=S_2/S\times 100\%$;

the proportion of the total area of the broken particles in the total area of the particles $A=S_2/S_1\times 100\%$; and the proportion of the total area of particles $B=(S-S_1-S_3)/S\times 100\%-P$.

3. Porosity test on the positive electrode

A real density tester AccuPyc II 1340 was used for testing. Each sample was measured at least three times, and at least 3 pieces of data were selected to take an average value. The porosity P of the positive electrode was calculated according to the formula $P=(V1-V2)/V1\times 100\%$, where V1 was the apparent volume, V1=sample surface area×sample thickness×number of samples; and V2 was the real volume.

4. Scanning electron microscope (SEM) test on the positive electrode of the lithium-ion battery After the lithium-ion battery reached a fully discharged state (that is, discharged to a cut-off voltage of 2.8V), the battery was disassembled to obtain the positive electrode. The positive electrode was cleaned with DMC and dried in vacuum, and then cut off along the direction of the positive electrode plate, and the interface of the positive active material was tested by SEM.

5. Cycle performance test on the lithium-ion battery (1). Cycle Performance Test on the Lithium-Ion Battery The lithium ion battery was placed in a 45° C. thermostat and stood for 30 minutes to bring the lithium ion battery to a constant temperature. The lithium-ion battery that had reached a constant temperature was charged at a constant current of 1 C to a voltage of 4.2V, then charged at a constant voltage of 4.2V to a current of 0.05 C, and then discharged at a constant current of 4 C to a voltage of 2.8V. This was one charge-discharge cycle. The first discharge capacity was 100%. The battery was charged and discharged for 600 cycles, and then the test was stopped. A post-cycle capacity retention rate was recorded as an index for evaluating the cycle performance of the lithium-ion battery.

The post-cycle capacity retention rate was the capacity after 600 cycles divided by the capacity at the first discharge.

Post-cycle thickness change was thickness of the battery after 600 cycles minus an initial thickness of the battery, and then divided by the initial thickness of the battery.

(2) High-temperature storage performance test on the lithium-ion battery after cycling The lithium-ion battery was charged to 4.2 V at a constant current of 1 C, and then charged to a current of 0.05 C at a constant voltage. The fully charged battery after cycling was placed in a 60° C. thermostat, and stored there for 30 days. Then, the thickness change from before to after storage was recorded.

Thickness change=(thickness after 30 days storage/initial thickness−1)×100%.

A. The lithium ion batteries of Comparative Example 1-1 to Comparative Example 1-3, and Example 1-1 to Example 1-33 were prepared according to the above methods, and the cycle performance and the high-temperature storage performance after cycling of the lithium-ion batteries were tested. Test results of the batteries with different amounts of substances added to the electrolyte were shown in Table.

TABLE 1

| | Compound of Formula I | | $LiPO_2F_2$ | Additive B | Cycle performance | | High-temperature storage |
|---|---|---|---|---|---|---|---|
| | Type | Added amount* (g) | Added amount* (g) | Added amount* (g) | Capacity Retention rate | Thickness Change | Thickness Change |
| Comparative Example 1-1 | \ | \ | \ | \ | 72.50% | 23.76% | 43.55% |
| Comparative Example 1-2 | \ | \ | 0.0001 | \ | 74.87% | 21.33% | 38.51% |
| Comparative Example 1-3 | \ | \ | \ | \ | 71.30% | 25.62% | 45.17% |
| Example 1-1 | Compound I-1 | 0.001 | \ | \ | 79.02% | 15.00% | 30.81% |
| Example 1-2 | Compound I-1 | 0.01 | \ | \ | 80.71% | 13.43% | 25.93% |
| Example 1-3 | Compound I-1 | 0.015 | \ | \ | 81.23% | 13.13% | 20.33% |
| Example 1-4 | Compound I-1 | 0.03 | \ | \ | 82.21% | 12.92% | 16.16% |
| Example 1-5 | Compound I-1 | 0.046 | \ | \ | 81.95% | 12.32% | 15.63% |
| Example 1-6 | Compound I-1 | 0.01 | 0.000026 | \ | 81.63% | 12.05% | 20.48% |
| Example 1-7 | Compound I-1 | 0.01 | 0.0003 | \ | 83.02% | 11.87% | 18.72% |
| Example 1-8 | Compound I-1 | 0.01 | 0.001 | \ | 84.06% | 11.63% | 18.02% |
| Example 1-9 | Compound I-1 | 0.01 | 0.005 | \ | 84.43% | 11.51% | 16.85% |
| Example 1-10 | Compound I-1 | 0.01 | 0.01 | \ | 85.05% | 10.72% | 15.21% |
| Example 1-11 | Compound I-1 | 0.01 | 0.019 | \ | 85.20% | 10.11% | 14.59% |
| Example 1-12 | Compound I-2 | 0.01 | 0.001 | \ | 83.35% | 11.48% | 18.23% |
| Example 1-13 | Compound I-3 | 0.01 | 0.001 | \ | 83.88% | 11.53% | 17.92% |
| Example 1-14 | Compound I-4 | 0.01 | 0.001 | \ | 83.04% | 11.22% | 18.55% |
| Example 1-15 | Compound I-1 | 0.01 | 0.005 | 0.005 g TECP | 86.21% | 9.57% | 14.83% |
| Example 1-16 | Compound I-1 | 0.01 | 0.005 | 0.0005 g VC + 0.002 g FEC | 86.42% | 9.60% | 13.43% |
| Example 1-17 | Compound I-1 | 0.01 | 0.005 | 0.002 g FEC + 0.008 g HTCN | 86.70% | 9.78% | 10.86% |
| Example 1-18 | Compound I-1 | 0.01 | 0.03 | 0.002 g FEC + 0.003 g HTCN | 87.81% | 10.63% | 13.17% |
| Example 1-19 | Compound I-1 + Compound I-2 | 0.005 + 0.05 | 0.005 | 0.0005 g VC + 0.002 g FEC | 86.41% | 10.17% | 12.60% |
| Example 1-20 | Compound I-1 + Compound I-3 | 0.005 + 0.05 | 0.005 | 0.0005 g VC + 0.002 g FEC | 86.45% | 9.86% | 12.52% |
| Example 1-21 | Compound I-1 | 0.01 | \ | 0.002 g FEC + 0.003 g HTCN | 86.81% | 10.63% | 13.17% |
| Example 1-22 | Compound I-1 | 0.01 | 0.005 | 0.0005 g VC + 0.002 g FEC | 87.85% | 9.52% | 12.57% |
| Example 1-23 | Compound I-1 | 0.01 | 0.005 | 0.0005 g VC + 0.002 g FEC | 89.02% | 9.38% | 11.34% |
| Example 1-24 | Compound I-1 | 0.01 | 0.005 | 0.0005 g VC + 0.002 g FEC | 87.55% | 9.48% | 12.51% |
| Example 1-25 | Compound I-1 | 0.01 | \ | \ | 78.95% | 13.31% | 25.63% |
| Example 1-26 | Compound I-1 | 0.01 | \ | \ | 79.82% | 11.81% | 18.84% |
| Example 1-27 | Compound I-1 | 0.01 | \ | \ | 77.12% | 14.10% | 28.56% |
| Example 1-28 | Compound I-1 | 0.01 | \ | \ | 79.45% | 12.90% | 20.41% |
| Example 1-29 | Compound I-1 | 0.01 | \ | \ | 73.71% | 15.43% | 27.93% |
| Example 1-30 | Compound I-1 | 0.01 | 0.005 | 0.0005 g VC + 0.002 g FEC | 80.11% | 13.34% | 19.17% |
| Example 1-31 | Compound I-1 + Compound I-2 | 0.05 + 0.05 | \ | \ | 73.51% | 14.42% | 27.80% |
| Example 1-32 | Compound I-1 + Compound I-4 | 0.05 + 0.05 | \ | \ | 82.67% | 13.32% | 24.83% |
| Example 1-33 | Compound I-1 | 0.01 | \ | \ | 84.52% | 13.41% | 24.82% |

Note:

"/" indicates being not added; and (2)

*the added amount is the number of grams that need to be added per 1 g of the positive active material.

According to the comparison between Examples 1-1 to 1-5 and Comparative Examples 1-1 to 1-2, it can be seen that the cycle performance and high-temperature storage performance of lithium-ion batteries can be significantly improved by adding a particular amount of the compound of Formula I in the electrolyte. This may be mainly because the compound of Formula I could form a film on the surface of the positive-electrode material and reduce the occurrence of side reactions.

According to the comparison between Examples 1-6 to 1-14 and Example 1-2, it can be seen that the cycle performance and high-temperature storage performance of lithium-ion batteries can be further improved by further adding a particular amount of additive A (for example, $LiPF_2O_2$) to the electrolyte containing the compound of Formula I (for example, at least one of compounds 1-1, 1-2, 1-3 or 1-4). The reason for this improvement may be that additive A (for example, $LiPF_2O_2$) formed a film preferentially on the surface of the negative electrode, improved the film-forming structure and enhanced the film-forming stability, which was conducive for the compound of Formula I to play a greater role in the late stage of cycling.

According to the comparison between Examples 1-15 to 1-20 and Example 1-9, it can be seen that the cycle performance and high-temperature storage performance of lithium-ion batteries can be further improved by further adding a particular amount of additive B to the electrolyte containing appropriate amounts of the compound of Formula I and the additive A (for example, $LiPF_2O_2$). According to the comparison between Example 1-21 and Example 1-2, it can be seen that the cycle performance and high-temperature storage performance of lithium-ion batteries can be further improved by further adding a particular amount of additive B to the electrolyte containing an appropriate amount of the compound of Formula I. This may be mainly because the additive B acted on film forming of the negative electrode during chemical conversion, which enhanced the interface stability of the negative electrode.

According to the comparison between Examples 1-22 to 1-24 and Example 1-16, it can be seen that the cycle performance and high-temperature storage performance of lithium-ion batteries can be further improved by further adding a particular amount of the compound of Formula II to the electrolyte containing appropriate amounts of the compound of Formula I, additive A and additive B. This may be mainly because the compound of Formula II reduced the viscosity of the electrolyte and the combination of additives changed the film-forming structure on the surface of the positive electrode, thus improving the film-forming stability.

According to the comparison between Example 1-25 and Example 1-2, it can be seen that the performance of the positive active material modified by the liquid phase mixing and the sol-gel method are close, and both methods are suitable for the modification of the positive active material.

According to the comparison between Examples 1-26 and 1-27 and Example 1-2, it can be seen that reducing the compacted density of the positive active material layer can improve the cycle performance and high-temperature storage performance. This may be because an appropriate compacted density could reduce particle breakage, and an increased compacted density could result in increased particle breakage. Considering the requirements for the mass energy density and the volume energy density in practical application, a compacted density <3.6 $g/cm^3$ is suitable for practical application.

According to the comparison between Example 1-28 and Example 1-2, it can be seen that controlling the proportion of the first particles in the positive active material could alleviate the side reactions caused by particle breakage at the late stage of cycling, which was beneficial to improve the cycle performance and high-temperature storage performance.

According to the comparison between Example 1-29 and Example 1-2, it can be seen that the stability of the positive-electrode material modified by $Li_3PO_4$ was improved, which effectively reduced the side reactions between the electrolyte and the positive electrode, and improved the cycle performance of the battery.

According to the comparison between Examples 1-31 and 1-30 and Example 1-29, it can be seen that in the case where the positive active material was not modified by $Li_3PO_4$, the cycle performance and high-temperature storage performance of the lithium-ion batteries can be further improved by further adding the additive A (for example, $LiPF_2O_2$) and the additive B to the electrolyte containing an appropriate amount of the compound of Formula I.

According to the comparison between Examples 1-33 and 1-32 and Example 1-2, it can be seen that the cycle performance and high-temperature storage performance of the batteries can be further improved when the element Q was contained in the positive active material.

B. The lithium-ion batteries of Comparative Example 2-1 to Comparative Example 2-4, and Example 2-1 to Example 2-18 were prepared according to the above methods, and the cycle performance and the high-temperature storage performance after cycling of the lithium-ion battery were tested. The positive active materials, electrolytes and test results are shown in Table 2 and table 3. The proportions of the cross-sectional areas of the first particles and the second particles in the positive active material was implemented by controlling a mass ratio of the first particles to the second particles.

TABLE 2

|  | Compound of formula I | | $LiPO_2F_2$ | |
|---|---|---|---|---|
|  | Type | Added amount* (g) | Added amount* (g) | Positive active material |
| Comparative Example 1-1 | \ | \ | \ | $Li_3PO_4$ modified $LiNi_{0.84}Co_{0.13}Mn_{0.06}O_2$ |
| Comparative Example 1-3 | \ | \ | \ | $LiNi_{0.84}Co_{0.13}Mn_{0.06}O_2$ |
| Comparative Example 2-1 | \ | \ | \ | $LiNi_{0.61}Co_{0.19}Mn_{0.20}O_2$ |
| Comparative Example 2-2 | \ | \ | \ | $LiNi_{0.84}Co_{0.13}Mn_{0.06}O_2$ |

TABLE 2-continued

| | | | | |
|---|---|---|---|---|
| Comparative Example 2-3 | \ | \ | \ | LiNi$_{0.84}$Co$_{0.13}$Mn$_{0.06}$O$_2$ |
| Comparative Example 2-4 | \ | \ | \ | LiNi$_{0.95}$Co$_{0.025}$Mn$_{0.025}$O$_2$ |
| Example 1-2 | Compound I-1 | 0.01 | \ | Li$_3$PO$_4$ modified LiNi$_{0.84}$Co$_{0.13}$Mn$_{0.06}$O$_2$ |
| Example 1-8 | Compound I-1 | 0.01 | 0.001 | Li$_3$PO$_4$ modified LiNi$_{0.84}$Co$_{0.13}$Mn$_{0.06}$O$_2$ |
| Example 2-1 | Compound I-1 | 0.01 | \ | Li$_3$PO$_4$ modified LiNi$_{0.61}$Co$_{0.19}$Mn$_{0.20}$O$_2$ |
| Example 2-2 | Compound I-1 | 0.01 | \ | Li$_3$PO$_4$ modified LiNi$_{0.61}$Co$_{0.19}$Mn$_{0.20}$O$_2$ |
| Example 2-3 | Compound I-1 | 0.01 | \ | Li$_3$PO$_4$ modified LiNi$_{0.84}$Co$_{0.13}$Mn$_{0.06}$O$_2$ |
| Example 2-4 | Compound I-1 | 0.01 | \ | Li$_3$PO$_4$ modified LiNi$_{0.95}$Co$_{0.025}$Mn$_{0.025}$O$_2$ |
| Example 2-5 | Compound I-1 | 0.01 | 0.001 | Li$_3$PO$_4$ modified LiNi$_{0.61}$Co$_{0.19}$Mn$_{0.20}$O$_2$ |
| Example 2-6 | Compound I-1 | 0.01 | 0.001 | Li$_3$PO$_4$ modified LiNi$_{0.95}$Co$_{0.025}$Mn$_{0.025}$O$_2$ |
| Example 2-7 | Compound I-1 | 0.01 | 0.001 | Li$_3$PO$_4$ modified LiNi$_{0.84}$Co$_{0.13}$Mn$_{0.06}$O$_2$ |
| Example 2-8 | Compound I-1 | 0.01 | 0.001 | Li$_3$PO$_4$ modified LiNi$_{0.84}$Co$_{0.13}$Mn$_{0.06}$O$_2$ |
| Example 2-9 | Compound I-1 | 0.01 | 0.001 | Li$_3$PO$_4$ modified LiNi$_{0.84}$Co$_{0.13}$Mn$_{0.06}$O$_2$ |
| Example 2-10 | Compound I-1 | 0.03 | 0.001 | Li$_3$PO$_4$ modified LiNi$_{0.61}$Co$_{0.19}$Mn$_{0.20}$O$_2$ |
| Example 2-11 | Compound I-1 | 0.01 | 0.001 | Li$_3$PO$_4$ modified LiNi$_{0.84}$Co$_{0.13}$Mn$_{0.06}$O$_2$ |
| Example 2-12 | Compound I-1 | 0.01 | 0.001 | Li$_3$PO$_4$ modified LiNi$_{0.84}$Co$_{0.13}$Mn$_{0.06}$O$_2$ |
| Example 2-13 | Compound I-1 + Compound I-2 | 0.005 + 0.005 | 0.001 | Li$_3$PO$_4$ modified LiNi$_{0.84}$Co$_{0.13}$Mn$_{0.06}$O$_2$ |
| Example 2-14 | Compound I-1 + Compound I-2 | 0.005 + 0.005 | 0.001 | Li$_3$PO$_4$ modified LiNi$_{0.84}$Co$_{0.13}$Mn$_{0.06}$O$_2$ |
| Example 1-32 | Compound I-1 + Compound I-4 | 0.05 + 0.05 | \ | LiNi$_{0.84}$Co$_{0.13}$Mn$_{0.058}$Zr$_{0.002}$O$_2$ |
| Example 2-15 | Compound I-1 + Compound I-4 | 0.05 + 0.05 | \ | Li$_3$PO$_4$ modified LiNi$_{0.84}$Co$_{0.13}$Mn$_{0.058}$Zr$_{0.002}$O$_2$ |
| Example 2-16 | Compound I-1 + Compound I-4 | 0.05 + 0.05 | 0.001 | Li$_3$PO$_4$ modified LiNi$_{0.84}$Co$_{0.13}$Mn$_{0.058}$Zr$_{0.002}$O$_2$ |
| Example 2-17 | Compound I-1 + Compound I-4 | 0.05 + 0.05 | 0.001 | Li$_3$PO$_4$ modified LiNi$_{0.84}$Co$_{0.13}$Mn$_{0.058}$Zr$_{0.002}$O$_2$ |
| Example 2-18 | Compound I-1 + Compound I-4 | 0.05 + 0.05 | 0.001 | Li$_3$PO$_4$ modified LiNi$_{0.84}$Co$_{0.13}$Mn$_{0.058}$Zr$_{0.02}$O$_2$ |

| | Proportion of cross-sectional area of first particles | Proportion of cross-sectional area of second particles | Compacted density of positive active material layer g/cm$^3$ | Cycle performance | | High-temperature storage Thickness Change |
|---|---|---|---|---|---|---|
| | | | | Capacity retention rate | Thickness Change | |
| Comparative Example 1-1 | 27.1% | 37.8% | 3.4 | 72.50% | 23.76% | 43.55% |
| Comparative Example 1-3 | 27.1% | 37.8% | 3.4 | 71.30% | 25.62% | 45.17% |
| Comparative Example 2-1 | 23.4% | 41.3% | 3.4 | 75.96% | 18.91% | 30.94% |
| Comparative Example 2-2 | 27.2% | 38.1% | 3.4 | 71.85% | 24.02% | 44.33% |
| Comparative Example 2-3 | 0% | 64.8% | 3.4 | 70.36% | 26.58% | 49.28% |
| Comparative Example 2-4 | 25.3% | 40.2% | 3.4 | 69.02% | 26.76% | 53.42% |
| Example 1-2 | 27.1% | 37.8% | 3.4 | 80.71% | 13.43% | 25.93% |
| Example 1-8 | 27.1% | 37.8% | 3.4 | 84.06% | 11.63% | 18.02% |
| Example 2-1 | 0% | 65.5% | 3.4 | 80.64% | 14.28% | 20.54% |
| Example 2-2 | 23.4% | 41.3% | 3.4 | 84.87% | 12.58% | 16.63% |
| Example 2-3 | 0% | 64.8% | 3.4 | 77.53% | 12.36% | 26.85% |
| Example 2-4 | 25.3% | 40.2% | 3.4 | 76.92% | 15.38% | 30.87% |
| Example 2-5 | 23.4% | 41.3% | 3.4 | 88.12% | 11.79% | 11.35% |
| Example 2-6 | 25.3% | 40.2% | 3.4 | 80.89% | 15.02% | 16.84% |
| Example 2-7 | 40.1% | 24.2% | 3.4 | 83.56% | 10.93% | 16.02% |
| Example 2-8 | 30.5% | 35.3% | 3.4 | 83.97% | 10.74% | 14.53% |
| Example 2-9 | 13.5% | 52.3% | 3.4 | 85.37% | 10.37% | 13.76% |
| Example 2-10 | 23.4% | 41.3% | 3.4 | 86.92% | 11.82% | 14.53% |
| Example 2-11 | 24.5% | 40.7% | 3.3 | 85.06% | 10.58% | 17.13% |

TABLE 2-continued

| Example 2-12 | 20.5% | 42.6% | 3.2 | 86.23% | 11.32% | 17.45% |
| Example 2-13 | 34.5% | 33.4% | 3.5 | 85.42% | 12.19% | 16.35% |
| Example 2-14 | 34.5% | 33.4% | 3.5 | 84.51% | 13.25% | 17.02% |
| Example 1-32 | 27.1% | 37.8% | 3.4 | 82.67% | 13.32% | 24.83% |
| Example 2-15 | 18.6% | 46.1% | 3.4 | 83.15% | 13.46% | 23.25% |
| Example 2-16 | 18.6% | 46.1% | 3.4 | 88.32% | 9.73% | 15.23% |
| Example 2-17 | 0% | 65.3% | 3.4 | 78.32% | 19.43% | 30.23% |
| Example 2-18 | 61.4% | 0% | 3.4 | 78.42% | 23.43% | 32.43% |

Note:
"/" indicates being not added; and (2)
*the added amount is the number of grams that need to be added per 1 g of the positive active material.

According to the comparison between Comparative Examples 2-1 to 2-4 and Examples 2-1 to 2-4, it can be seen that the use of various nickel-rich positive-electrode materials modified by $Li_3PO_4$ and the addition of the compound of Formula I in the electrolyte can stabilize the material structure, stabilize the interface with the electrolyte, reduce side reactions, and thus further improve the cycle performance and high-temperature storage performance of the lithium-ion batteries. According to Examples 2-5 to 2-9 and Examples 2-11 to 2-13, it can be further seen that the use of various nickel-rich positive-electrode materials modified by $Li_3PO_4$ and the addition of the compound of Formula I and the additive A (for example, LiPO2F2) in the electrolyte can further improve the cycle performance and high-temperature storage performance of the lithium-ion batteries. This may be mainly because the addition of the additive A brought down the film-forming resistance, thus reducing the DC internal resistance of the battery and reducing the side reactions of the electrolyte on the surface of the positive electrode.

According to Examples 2-15 to 2-18 and Examples 1-32, it can be further seen that when the nickel content in the positive electrode active material was relatively high, especially when the molar content of nickel was not less than 60%, the amount of the first particles and the amount of the second particles in the positive-electrode material within proper ranges were beneficial to the improvement of cycle performance and the alleviation of gas generation.

Without wishing to be bound by any theory, it is found in the present application that adding the compound of Formula I (for example, 1, 3-propane sultone (PS)) as a positive film-forming additive in the electrolyte could improve interface stability and reduce side reactions; in addition, it is found that the modification to the grain boundary of the secondary particles could significantly inhibit the particle breakage during the cycling of nickel-rich ternary positive-electrode materials, thus improving the stability of the material structure. The use of additive A (for example, $LiPO_2F_2$) in the electrolyte could cause a solid electrolyte interface film (SEI) formed on the positive electrode to have the effect of fast ion conduction, which was beneficial to reduce the direct current resistance (DCR) and increase the inorganic components in the film formation on the electrode interface, thereby enhancing the stability of the interface protection layer and protecting the positive electrode interface. The smaller primary particles in the positive-electrode material were beneficial to shorten the ion transmission distance and improve the rate performance of the material, and the smaller primary particles could increase the specific surface area of the material and increase the consumption of film-forming additives. The further introduction of the compound of Formula II (such as a fluorinated solvent) into the electrolyte could increase the stability of the electrolyte and reduce reactions of the solvent on the surface of the material.

The particle size and specific surface area of the positive-electrode material could be limited by the combination of grain boundary modification of the positive-electrode material and the additives to of the electrolyte for protection of the positive electrode. This, could ensure the rate performance of the battery, and also effectively improve the high-temperature storage and high-temperature cycling of the spherical secondary particle nickel-rich ternary material battery system, and solve the gassing problem during high-temperature cycling.

C. Scanning electron microscope (SEM) test on the positive active material

The positive active material of Comparative Example 1-1 ($Li_3PO_4$ modified $LiNi_{0.84}Co_{0.13}Mn_{0.06}O_2$) was tested by a scanning electron microscope, and the result is shown in FIG. 1.

In FIG. 1, the left picture shows a SEM image of the positive active material, and the right picture shows a distribution diagram of the phosphorus content in the SEM image. It can be seen from the right picture that phosphorous was distributed on the surface or grain boundary of the positive active material, as indicated by gray dots.

The SEM test results of the modified positive active material in other examples were similar to FIG. 1.

The above are only a few embodiments of the present invention, which do not limit the present invention in any form. Although the present invention is disclosed as above with preferred embodiments, these embodiments are not intended to limit the present invention. Changes or modifications made by those skilled in the art using the technical content disclosed above without departing from the scope of the technical solution of the present invention are considered as equivalent embodiments and fall within the scope of the technical solution.

References to "some embodiments", "an embodiment", "another example", "examples", "specific examples", or "some examples" in the specification mean the inclusion of specific features, structures, materials, or characteristics described in the embodiment or example in at least one embodiment or example of the application. Accordingly, descriptions appearing in the specification, such as "in some embodiments", "in the embodiments", "in an embodiment", "in another example", "in an example", "in a particular example", or "for example", are not necessarily references to the same embodiments or examples in the application. In addition, specific features, structures, materials, or characteristics herein may be incorporated in any suitable manner into one or more embodiments or examples. Although illustrative embodiments have been demonstrated and described, those skilled in the art should understand that the above embodiments are not to be construed as limiting the application, and that the embodiments may be changed, replaced, and modified without departing from the spirit, principle, and scope of the application.

What is claimed is:

1. An electrochemical apparatus, comprising a positive electrode, a negative electrode, a separator, and an electrolyte, wherein
the positive electrode comprises a current collector and a positive active material layer, and the positive active material layer comprises a positive active material; and
the electrolyte comprises a compound of Formula I:

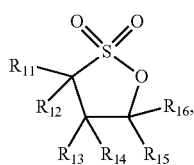

Formula I wherein $R_{11}$, $R_{12}$, $R_{13}$, $R_{14}$, $R_{15}$ and $R_{16}$ are each independently selected from: H, halogen, and the following substituted or unsubstituted groups: a $C_{1-8}$ alkyl group, a $C_{2-8}$ alkenyl group, a $C_{2-8}$ alkynyl group, or a $C_{6-12}$ aryl group; and
an amount of the compound of Formula I required per 1 g of the positive active material is about 0.001 g to about 0.064 g;
wherein the electrolyte further comprises an additive A and an additive B,
the additive A comprises at least one of $LiBF_4$, $LiPO_2F_2$, LiFSI, LiTFSI, 4,5-dicyano-2-(trifluoromethyl)imidazole, lithium difluoro bis(oxalate) phosphate, lithium difluoro(3 xalate) borate, or lithium bisoxalate borate,
the additive B comprises at least one of 1,3,5-pentanetricarbonitrile, 1,3,6-hexanetricarbonitrile, 1,2,6-hexanetricarbonitrile, or 1,2,3-tris(2-cyanoethoxy)propane, and
an amount of the additive A is 0.000026 g to 0.019 g per 1 g of the positive active material, and an amount of the additive B is 0.0001 g to 0.2 g per 1 g of the positive active material;
wherein the electrolyte further comprises a compound of formula II

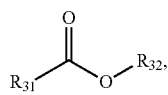

Formula II wherein $R_{31}$ and $R_{32}$ are each independently selected from a substituted or unsubstituted $C_{1-10}$ alkyl group, or a substituted or unsubstituted $C_{2-8}$ alkenyl group, wherein being substituted refers to substitution with one or more halogen atoms; and
based on a total weight of the electrolyte, a content of the compound of formula II is 10 wt % to 50 wt %.

2. The electrochemical apparatus according to claim 1, wherein the compound of Formula I comprises at least one of the following compounds:

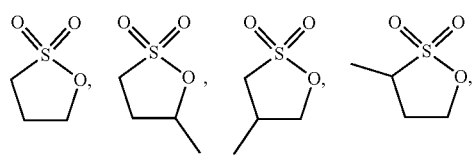

-continued

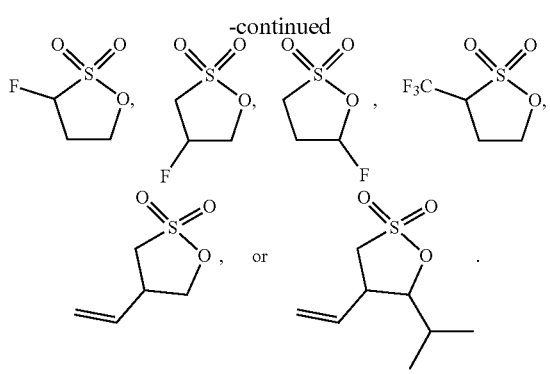

3. The electrochemical apparatus according to claim 1, wherein the positive active material layer comprises first particles, and a roundness of the first particles is 0.4 to 1, and with respect to a cross-sectional area of the positive electrode perpendicular to a direction of the current collector, a cross-sectional area of the first particle is greater than or equal to 20 square microns, and a sum of the cross-sectional areas of the first particles is 5% to 50% of a cross-sectional area of positive electrode.

4. The electrochemical apparatus according to claim 3, wherein the active material layer comprises second particles, and a roundness of the second particles is less than 0.4, and with respect to the cross-sectional area of the positive electrode perpendicular to the direction of the current collector, a cross-sectional area of the second particle is less than the cross-sectional area of the first particle, and a sum of the cross-sectional areas of the second particles is 5% to 60% of a cross-sectional area of positive electrode.

5. The electrochemical apparatus according to claim 1, wherein the additive B further comprises at least one of vinylene carbonate, fluoroethylene carbonate, ethylene sulfate, tris(trimethylsilyl) phosphate, tris(trimethylsilyl) borate, adiponitrile, or succinonitrile.

6. The electrochemical apparatus according to claim 5, wherein a mass ratio of the compound of formula I to the additive B is 7:1 to 1:7.

7. The electrochemical apparatus according to claim 1, wherein the positive active material layer comprises a phosphorus-containing compound, and the phosphorus-containing compound comprises at least one of $Li_3PO_4$ or $LiMPO_4$, wherein M is selected from at least one of Co, Mn, or Fe.

8. The electrochemical apparatus according to claim 7, wherein the phosphorous-containing compound is contained in a surface or a grain boundary of the positive active material.

9. The electrochemical apparatus according to claim 1, wherein the positive active material comprises $LiNi_xCo_yMn_zO_2$, wherein $0.55<x<0.92$, $0.03<y<0.2$, and $0.04<z<0.3$.

10. The electrochemical apparatus according to claim 1, wherein a compacted density of the positive active material layer is greater than 0 and less than or equal to 3.6 g/cm³.

11. The electrochemical apparatus according to claim 1, wherein the compound of formula II comprises at least one of the following compounds:

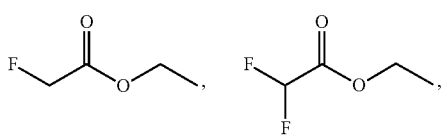

-continued

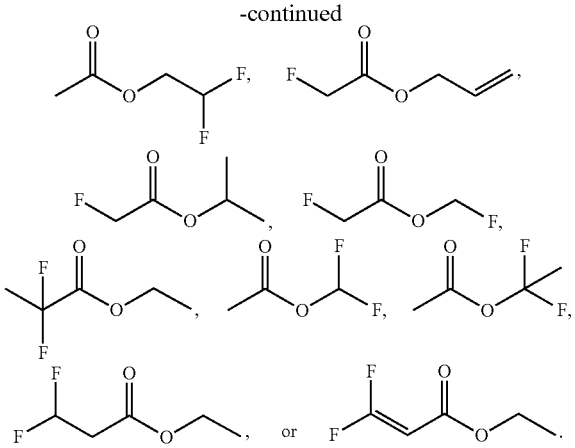

12. An electronic apparatus, comprising an electrochemical apparatus, where in the electrochemical apparatus comprises a positive electrode, a negative electrode, a separator, and an electrolyte, wherein
the positive electrode comprises a current collector and a positive active material layer, and the positive active material layer comprises a positive active material; and
the electrolyte comprises a compound of Formula I:

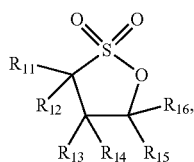

Formula I wherein $R_{11}$, $R_{12}$, $R_{13}$, $R_{14}$, $R_{15}$ and $R_{16}$ are each independently selected from: H, halogen, and the following substituted or unsubstituted groups: a $C_{1-8}$ alkyl group, a $C_{2-8}$ alkenyl group, a $C_{2-8}$ alkynyl group, or a $C_{6-12}$ aryl group; and
an amount of the compound of Formula I per 1 g of the positive active material is about 0.001 g to about 0.064 g;
wherein the electrolyte further comprises an additive A and an additive B,
the additive A comprises at least one of $LiBF_4$, $LiPO_2F_2$, LiFSI, LiTFSI, 4,5-dicyano-2-(trifluoromethyl)imidazole, lithium difluoro bis(oxalate) phosphate, lithium difluoro(7 xalate) borate, or lithium bisoxalate borate,
the additive B comprises at least one of 1,3,5-pentanetricarbonitrile, 1,3,6-hexanetricarbonitrile, 1,2,6-hexanetricarbonitrile, or 1,2,3-tris(2-cyanoethoxy)propane, and
an amount of the additive A is 0.000026g to 0.019 g per 1 g of the positive active material, and an amount of the additive B is 0.0001g to 0.2 g per 1 g of the positive active material;

wherein the electrolyte further comprises a compound of formula II

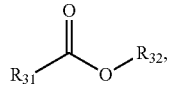

Formula II wherein $R_{31}$ and $R_{32}$ are each independently selected from a substituted or unsubstituted $C_{1-10}$ alkyl group, or a substituted or unsubstituted $C_{2-8}$ alkenyl group, wherein being substituted refers to substitution with one or more halogen atoms; and
based on a total weight of the electrolyte, a content of the compound of formula II is 10 wt % to 50 wt %.

13. The electronic apparatus according to claim 12, wherein the compound of Formula I comprises at least one of the following compounds:

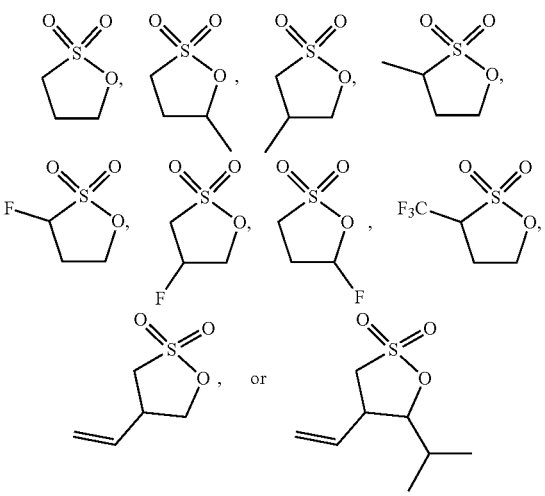

14. The electronic apparatus according to claim 12, the positive active material layer comprises first particles, and a roundness of the first particles is 0.4 to 1, and with respect to a cross-sectional area of the positive electrode perpendicular to a direction of the current collector, a cross-sectional area of the first particle is greater than or equal to 20 square microns, and a sum of the cross-sectional areas of the first particles is 5% to 50% of a cross-sectional area of positive electrode.

15. The electronic apparatus according to claim 14, wherein the active material layer comprises second particles, and a roundness of the second particles is less than 0.4, and with respect to the cross-sectional area of the positive electrode perpendicular to the direction of the current collector, a cross-sectional area of the second particle is less than the cross-sectional area of the first particle, and a sum of the cross-sectional areas of the second particles is 5% to 60% of the cross-sectional area of positive electrode.

* * * * *